(12) United States Patent
Olbert et al.

(10) Patent No.: US 7,837,856 B2
(45) Date of Patent: Nov. 23, 2010

(54) REACTOR FOR CARRYING OUT A CONTINUOUS OXYDEHYDROGENATION AND PROCESS

(75) Inventors: Gerhard Olbert, Dossenheim (DE); Franz Corr, Ludwigshafen (DE); Sven Crone, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 442 days.

(21) Appl. No.: 11/959,067

(22) Filed: Dec. 18, 2007

(65) Prior Publication Data
US 2008/0214883 A1    Sep. 4, 2008

Related U.S. Application Data

(60) Provisional application No. 60/870,715, filed on Dec. 19, 2006.

(30) Foreign Application Priority Data

Dec. 19, 2006    (DE) ........................ 10 2006 060 509

(51) Int. Cl.
| | |
|---|---|
| C10G 55/02 | (2006.01) |
| C10G 51/02 | (2006.01) |
| C10G 35/10 | (2006.01) |
| B01J 8/04 | (2006.01) |
| B01J 35/02 | (2006.01) |
| B01J 8/08 | (2006.01) |
| F28D 7/00 | (2006.01) |
| B01F 5/04 | (2006.01) |
| F28F 1/00 | (2006.01) |

(52) U.S. Cl. .................. 208/49; 208/176; 422/188; 422/200; 422/201; 422/218; 137/896; 165/177

(58) Field of Classification Search .............. 422/188, 422/200, 201, 218, 220; 208/49, 176; 137/896; 165/177; 585/412, 628, 654
See application file for complete search history.

(56) References Cited

U.S. PATENT DOCUMENTS

| 1,987,905 A | * | 1/1935 | Houdry | 422/198 |
| 4,594,227 A | * | 6/1986 | Ohsaki et al. | 422/148 |
| 4,869,808 A | * | 9/1989 | Vora et al. | 208/138 |

* cited by examiner

*Primary Examiner*—Walter D Griffin
*Assistant Examiner*—Natasha Young
(74) *Attorney, Agent, or Firm*—Oblon, Spivak, McClelland, Maier & Neustadt, L.L.P.

(57) ABSTRACT

A reactor for carrying out a continuous oxydehydrogenation of a feed gas stream of saturated hydrocarbons after premixing with an oxygen-comprising gas stream over a moving catalyst bed which is introduced in the longitudinal direction of their reactor between two concentric cylindrical holding devices so as to leave a central interior space and an intermediate space between the moving catalyst bed and the interior wall of the reactor to give a reaction gas mixture, wherein the reactor has two or more reactor sections which are separated from one another by disk-shaped deflection plates arranged alternately in the central interior space and divided in subregions by annular deflection plates arranged in the intermediate space between the moving catalyst bed and the interior wall of the reactor, in each case with a mixing-in device which is located upstream of the moving catalyst bed in the flow direction of the reaction gas mixture and comprises the following elements:

Figure 1:
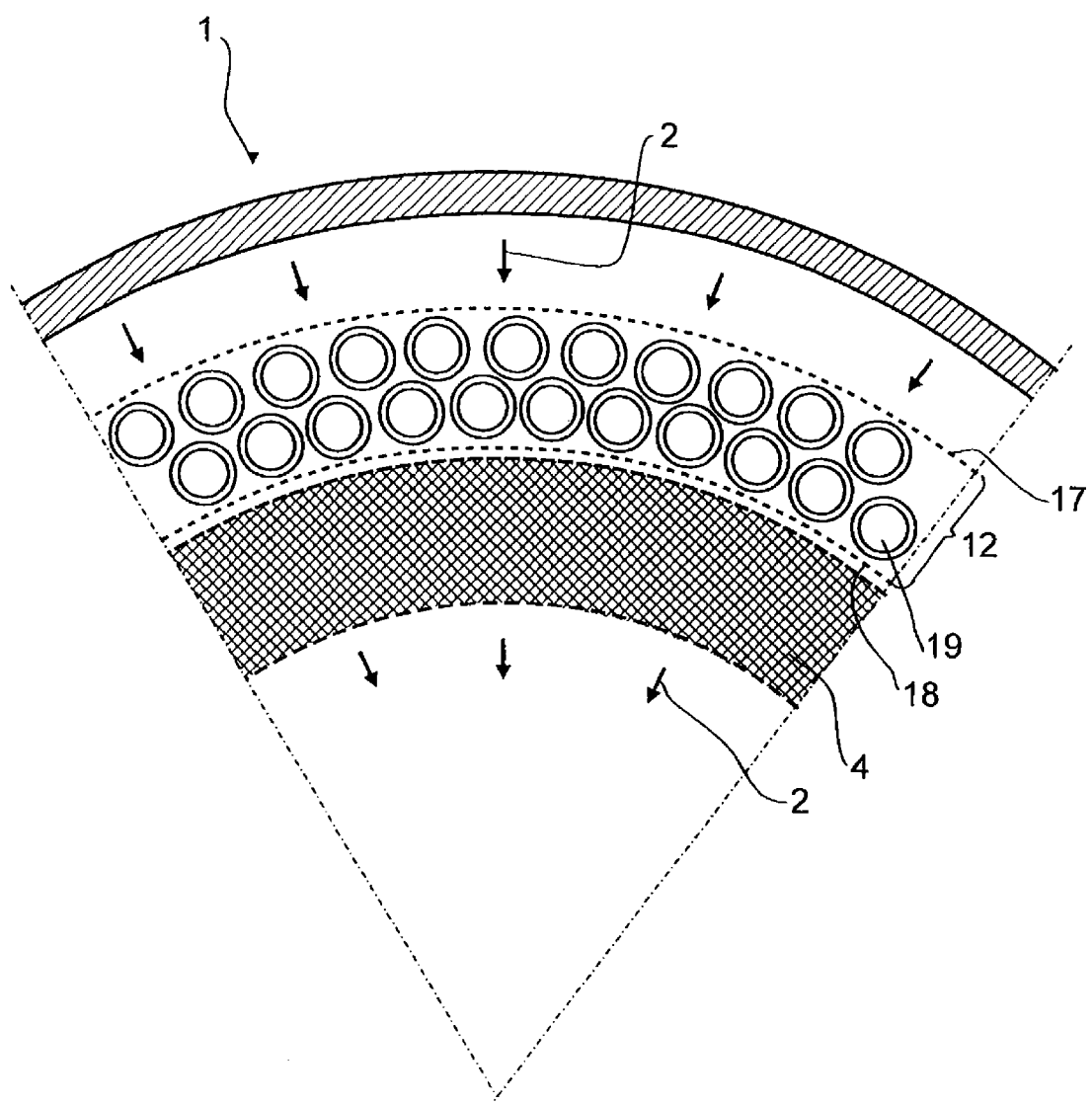

two or three rows arranged behind one another of tubes which have turbulence generators on their outside and constrict the flow cross section for the feed gas stream to from ½ to ¹⁄₁₀ of the free flow cross section, with the oxygen-comprising gas stream being passed through the interior spaces of the tubes and being injected via openings in the tubes into the feed gas stream, and a perforated plate upstream of the tubes and a perforated plate downstream of the tubes, is proposed.

26 Claims, 9 Drawing Sheets

REACTOR FOR CARRYING OUT A CONTINUOUS OXYDEHYDROGENATION AND PROCESS

The invention relates to a reactor for carrying out a continuous oxydehydrogenation of a feed gas stream of saturated hydrocarbons and a process for carrying out a continuous oxydehydrogenation in the reactor.

Oxydehydrogenations are carried out on a large scale in chemical engineering to upgrade paraffin-comprising hydrocarbon streams to the corresponding olefins. Since the reaction is endothermic, heat has to be introduced from the outside. Industrial oxydehydrogenations are, for example, the oxydehydrogenation of propane or the oxydehydrogenation of butane.

In the process known as the UOP Oleflex process for the dehydrogenation of propane to propene, a propane-comprising feed gas stream is preheated to an elevated temperature of frequently from 700 to 750° C. and dehydrogenated over a catalyst comprising platinum onto aluminum oxide in moving-bed dehydrogenation reactors to give a product gas stream comprising predominantly propane, propene and hydrogen. In the UOP Oleflex process, the heat of reaction necessary for the endothermic reaction is introduced via intermediate heaters, with a series arrangement of four intermediate heaters each with a downstream adiabatically operated reactor frequently being provided. A disadvantage here is, in particular, the high capital cost of the intermediate heaters; in addition, the stepwise indirect heat transfer necessitates a higher energy input and heating of the feed gas stream to higher temperatures, with correspondingly increased secondary reactions compared to direct heat transfer.

Direct heat transfer is employed in the autothermal BASF process in which part of the paraffin-comprising feed gas stream and also part of the hydrogen formed in the oxydehydrogenation are burnt to provide the heat required for the endothermic reaction. Advantages are the improved utilization of energy and also the fact that lower temperatures, with correspondingly lower stress on the feed gas stream, are necessary in the case of direct heat transfer. The autothermal BASF process generally requires two fixed-bed reactors which are operated alternately in the oxydehydrogenation mode and the regeneration mode, associated with a corresponding capital cost.

In the light of the above, it was an object of the invention to provide a reactor and a process for carrying out oxydehydrogenations of saturated hydrocarbons, which combine the advantages of known reactors and processes, in particular the advantages of the moving catalyst bed in the UOP Oleflex process and the energy advantages of the autothermal BASF process.

The invention accordingly provides a reactor for carrying out a continuous oxydehydrogenation of a feed gas stream of saturated hydrocarbons after premixing with an oxygen-comprising gas stream over a moving catalyst bed which is introduced in the longitudinal direction of the reactor between two concentric cylindrical holding devices so as to leave a central interior space and an intermediate space between the moving catalyst bed and the interior wall of the reactor to give a reaction gas mixture, wherein the reactor has two or more reactor sections which are separated from one another by disk-shaped deflection plates arranged alternately in the central interior space and divided in subregions by annular deflection plates arranged in the intermediate space between the moving catalyst bed and the interior wall of the reactor, in each case with a mixing-in device which is located upstream of the moving catalyst bed in the flow direction of the reaction gas mixture and comprises the following elements:

two or three rows arranged behind one another of tubes which have turbulence generators on their outside and constrict the flow cross section for the feed gas stream to from ½ to ⅒ of the free flow cross section, with the oxygen-comprising gas stream being passed through the interior spaces of the tubes and being injected via openings in the channels between the fins of the tubes into the feed gas stream, and a perforated plate upstream of the tubes and a perforated plate downstream of the tubes and the reaction gas mixture is conveyed alternately from the central interior space into the intermediate space between the moving catalyst bed and the inner wall of the reactor and vice versa in successive reactor sections.

The turbulence generators arranged on the outside of the tubes can be structures of various geometries, but it is essential that they increase the turbulence in the fluids flowing around the tubes. They are preferably elements as are known for static mixers or as packing elements in distillation columns or, for example, are crossed strips of metal sheet.

The tubes provided with turbulence generators are preferably finned tubes. It has been found that the use of a specific mixing-in device which ensures largely homogeneous mixing in very short delay times of less than 150 ms or even less than 50 ms makes it possible for an oxygen-comprising gas to be fed in continuously in tailored amounts corresponding to the progress of the reaction over a moving catalyst bed.

In the mixing-in device the feed stream of saturated hydrocarbons and the oxygen-comprising stream are premixed. Premixing is understood in the present case as mixing prior to entrance into the catalyst bed.

As a result of the use of commercial finned tubes known as heat exchangers and slight modification of these by providing openings in the channels between the fins, the intermediate spaces of the channels between the fins are utilized as virtually ideal mixing chambers having high turbulence as a result of the feed gas stream being introduced essentially perpendicular to the finned tubes and an oxygen-comprising gas stream being injected through the interior spaces of the finned tubes via the openings in the channels into the feed gas stream.

The volume flows of the feed gas stream and the oxygen-comprising gas stream are generally very different, which makes the mixing task correspondingly more difficult: the flow of the oxygen-comprising gas can be, in particular, from 5 to 30% of the flow of the feed gas stream.

The catalyst is arranged between two concentric cylindrical holding devices which in a preferred embodiment can be edge slit screens and are filled from above, in particular via a stock container, and emptied in the lower region by means of suitable facilities in an upright, generally cylindrical, reactor. The free-flowing shaped catalyst bodies travel along in the reactor from the top downward between the cylindrical holding devices in continuous narrow gaps which extend over the total height of the reactor. The maximum linear dimensions of the gaps are preferably less than or equal to half the smallest external diameter of the shaped catalyst bodies and are preferably in the range from 0.75 to 2.00 mm, particularly preferably about 1.2 mm.

Between the individual reactor sections, the moving catalyst bed is provided with short sealed stretches whose length corresponds, in particular, to approximately one bed thickness in order to substantially suppress bypasses of the reaction gas mixture.

A preferred catalyst which selectively catalyzes the combustion of hydrogen comprises oxides and/or phosphates selected from the group consisting of the oxides and/or phosphates of germanium, tin, lead, arsenic, antimony and bismuth. A further preferred catalyst which catalyzes the combustion of hydrogen comprises a noble metal of transition group VIII and/or I.

The dehydrogenation catalysts used generally comprise a support and an active composition. The support generally comprises a heat-resistant oxide or mixed oxide. The dehydrogenation catalysts preferably comprise a metal oxide selected from the group consisting of zirconium dioxide, zinc oxide, aluminum oxide, silicon dioxide, titanium dioxide, magnesium oxide, lanthanum oxide, cerium oxide and mixtures thereof as support. In the case of mixtures, these can be physical mixtures or chemical mixed phases such as magnesium or zinc aluminum oxide mixed oxides. Preferred supports are zirconium dioxide and/or silicon dioxide, with particular preference being given to mixtures of zirconium dioxide and silicon dioxide.

The active composition of the dehydrogenation catalysts generally comprises one or more elements of transition group VIII, preferably platinum and/or palladium, particularly preferably platinum. In addition, the dehydrogenation catalysts can comprise one or more elements of main group I and/or II, preferably potassium and/or cesium. Furthermore, the dehydrogenation catalysts can comprise one or more elements of transition group II including the lanthanides and actinides, preferably lanthanum and/or cerium. Finally, the dehydrogenation catalysts can comprise one or more elements of main group III and/or IV, preferably one or more elements from the group consisting of boron, gallium, silicon, germanium, tin and lead, particularly preferably tin.

In a preferred embodiment, the dehydrogenation catalyst comprises at least one element of transition group VIII, at least one element of main group I and/or II, at least one element of main group III and/or IV and at least one element of transition group III including the lanthanides and actinides.

For example, it is possible, according to the invention, to use all dehydrogenation catalysts disclosed in WO 99/46039, U.S. Pat. No. 4,788,371, EP-A 705 136, WO 99/29420, U.S. Pat. No. 5,220,091, U.S. Pat. No. 5,430,220, U.S. Pat. No. 5,877,369, EP 0 117 146, DE-A 19937 106, DE-A 19937105 and DE-A 199 37 107. Particularly preferred catalysts for the above-described variants of the autothermal dehydrogenation of propane are the catalysts of examples 1, 2, 3 and 4 of DE-A 199 37 107.

Preference is given to using steam-resistant catalysts which can be transported pneumatically.

The autothermal dehydrogenation of propane is preferably carried out in the presence of steam. The added steam serves as heat transfer medium and aids the gasification of organic deposits on the catalysts, as a result of which carbonization of the catalysts is countered and the operating life of the catalysts is increased. The organic deposits are converted into carbon monoxide, carbon dioxide and possibly water.

Fresh and/or regenerated catalyst is fed in from the top, in particular via a stock container, and taken off at the lower end of the reactor laden with undesirable materials. The catalyst thus travels from the top downward through the reactor. The laden catalyst is, in particular, transported pneumatically into a separate regeneration tower and regenerated there by means of oxygen-comprising gas in a known manner, by depressurization, flushing, burning-off, recrystallization, pressing down and interconnection, and subsequently recirculated, likewise pneumatically to the top of the reactor.

The reaction gas mixture flows into the moving catalyst bed from the side of an inflow face of this and leaves the moving catalyst bed via an outflow face.

According to the invention, a mixing-in device for the starting materials to be reacted which comprises the following elements:
- two or three rows arranged behind one another of tubes provided with turbulence generators, preferably finned tubes, and
- a perforated plate upstream of the finned tubes and
- a perforated plate downstream of the finned tubes, is provided upstream of the inflow face of the moving catalyst bed.

Finned tubes are known in chemical engineering and are used, in particular, as heat exchanger tubes. Finned tubes and their production are described, for example, in DE-A 1 950 246 or DE-A 2 131 085.

A finned tube is formed by a tube, generally a metal tube, which has a cylindrical exterior to which elongated strips, viz. the fins, are attached along a longitudinal edge, generally by welding. The fins are frequently attached in a spiral or helical fashion onto the exterior of the tube, but can also be attached in the longitudinal direction of this. They normally have a smooth continuous surface but can also be perforated. They can be continuous but can also, advantageously, be cut with the exception of a fin base to form segments. Cut fins are particularly suitable for increasing the turbulence. The segments here can have various geometries, for example in the form of rectangles, trapezoids, etc. The cuts between the segments can be configured with or without removal of material. The segments can particularly advantageously be rotated or slanted at an angle to the fin base in order to increase the turbulence, in particular in the regions between the fins, viz. the channels, by means of an angle of incidence and accordingly improve the mixing action.

A dense arrangement of fins over the length of the tube is advantageous; in particular, from 100 to 300 turns of the fins can be provided per meter of tube length.

Tubes having an external diameter in the range from 25 to 150 mm, in particular from 20 to 50 mm, are advantageously used.

The fin height based on the external diameter of the tubes is advantageously in the range from $1/10$ to $1/2$.

The fin thickness can advantageously be from 0.3 to 1.5 mm.

In the case of cut fins, it is advantageous to form segments having a width of from 3 to 12 mm, preferably from 4 to 8 mm.

The tubes can have any cross section, for example circular, oval or polygonal, for example triangular.

The finned tubes are arranged parallel to one another in rows, with one row of finned tubes being arranged along a radius of a circle.

In the case of the present radial flow reactor having a radial flow direction of the reaction gas mixture, the moving catalyst bed is arranged in the form of a hollow cylinder having a wall thickness appropriate to the bed thickness in suitable accommodation devices as described above. The finned tubes are arranged along a circle concentric with the moving catalyst bed on the inflow side of the moving catalyst bed, which is alternately on the inside or outside.

It has been found that two or three rows of finned tubes are suitable for the mixing task according to the invention.

In a preferred embodiment the composition of the oxygen-comprising gas stream can be different in the individual rows of tubes with turbulence generators on their outside. Especially, it is possible to feed into the first row of tubes with turbulence generators an oxygen-comprising gas stream with a composition different to the stream fed into the second row of tubes with turbulence generators.

Here, it is advantageous to arrange the second row of finned tubes next to the gaps between the first and, in the case of three rows of tinned tubes, arrange the third row of finned tubes next to the gaps in the second row of finned tubes. A heat transfer medium can advantageously flow through the second row and, if appropriate, the third row of finned tubes. It is also possible for the second and, if appropriate, third rows of finned tubes to be formed by solid material of any cross section.

Finned tubes of the same geometry should be used within a row of finned tubes, but the geometry can also vary within the rows of finned tubes.

The finned tubes have in each case two diametrically opposite openings per channel of fins on the exterior of the tubes forming them in the channels between the fins; these openings are located at the positions which are closest to the respective adjacent finned tube in the row of finned tubes. The oxygen-comprising gas stream is injected through these openings in the channels between the fins into the feed gas stream. In this way, a large number of small-scale mixing chambers having a high turbulence are thus made available in the channels, in particular in the case of fins cut to form segments, with this effect being able to be increased further by slanted setting of the fin segments. An excellent quality of mixing in the micro range is achieved in this way.

A concentric plug-in tube having outflow openings arranged at appropriate intervals on the exterior, preferably in each case two openings arranged diametrically opposite one another can in each case be advantageously provided in the interior of the finned tubes in order to predistribute the oxygen-comprising gas stream over the length of the tube and thus also to ensure a largely equalized temperature of this.

The oxygen-comprising gas stream is preferably introduced uniformly into the finned tubes via a ring line as a main distributor and particularly preferably via two ring lines at each end thereof.

The rows of finned tubes are preceded by a perforated plate which is likewise arranged perpendicular to the inflow direction of the oxygen-comprising gas stream and thus essentially on a circle concentric with the rows of finned tubes.

The upstream perforated plate has openings whose total area based on the cross-sectional area of the inflow of the oxygen-comprising gas steam is preferably less than or equal to 0.5, in particular less than or equal to 0.3.

The upstream perforated plate is advantageously located at a distance from the inflow face of the first row of finned tubes which corresponds to from seven to twenty times the diameter of the openings in the upstream perforated plate.

The diameter of the openings in the upstream perforated plate is advantageously smaller than half of the clear spacing of the fins between two successive turns.

The mixing-in device has a second perforated plate which is located downstream in the outflow direction from the device and has openings whose diameter is greater than or equal to the diameter of the upstream perforated plate.

The thickness of the two perforated plates, viz. the upstream perforated plate and the downstream perforated plate, based on the diameter of the openings in the perforated plates, is preferably in the range from 0.75 to 2.0.

The downstream perforated plate is advantageously arranged at a distance of from 0.75 to 2.0 times the diameter of the finned tubes of the last row of finned tubes from the outflow plane of the last row of finned tubes.

The downstream perforated plate is advantageously located at a distance corresponding to from 5 to 20 times the diameter of the openings in the downstream perforated plate from the entry into the moving catalyst bed.

The material for all regions of the reactor which come into contact with the reaction gas mixture, in particular for the finned tubes and the perforated plates and also the interior wall of the reactor, is preferably noncarburizing steel.

The mixing-in device is arranged essentially transverse to the flow direction of the oxygen-comprising gas stream. This means that the oxygen-comprising gas stream is introduced perpendicular to the main face of the mixing-in device, which in the case of radial flow reactors is curved. However, the term essentially perpendicular also encompasses deviations from the normals of $\pm 5°$ or $\pm 10°$ or even $\pm 30°$.

The mixing-in device can at construction depths, i.e. a distance between the upstream perforated plate and the downstream perforated plate, in the range from 100 to 200 mm achieve excellent, virtually 100% mixing with a pressure drop for the feed gas stream in the order of 20 mbar and a pressure drop for the oxygen-comprising stream which for safety reasons alone has to be under at least slightly superatmospheric pressure, in the range from about 50 to 100 mbar.

An extremely large number of points of injection of the feed gas stream into the oxygen-comprising gas stream in the order of 10 000 points of injection per $m^2$ is achieved.

The invention also provides a process for carrying out continuous oxydehydrogenations in a reactor as described above.

The feed gas stream of saturated hydrocarbons can be, in particular, a gas stream comprising propane or butane.

An oxygen-comprising gas stream, in particular air or technical-grade oxygen, is injected continuously into the feed gas stream via the mixing-in device. A reaction gas mixture which comprises, in particular, unreacted saturated hydrocarbons together with the corresponding olefins and hydrogen is formed at the end of the first reactor section and this flows as feed gas stream into the next reactor section where a further oxygen-comprising gas stream is injected continuously. This procedure is repeated until the reaction gas mixture leaves the last reactor section. Here, the conversion of the saturated hydrocarbons even after the last reactor section is incomplete and is, for example, in the region of about 30%.

In a particular embodiment, a substream of the reaction gas mixture is mixed with fresh feed gas stream comprising saturated hydrocarbons and recycled to the reactor, into the first reactor section. The remaining substream of the reaction gas mixture is taken off as product stream.

In a further preferred embodiment, the reaction gas mixture leaving the last reactor section can be used for heat integration by being used for preheating the feed gas stream comprising saturated hydrocarbons by indirect heat exchange.

The reactor and the process display, in particular, a fully continuous flow of the reaction gas mixture, so that a uniform, constant product composition over time is achieved.

The regeneration of the catalyst is likewise effected continuously in a small apparatus specifically designed for this purpose and is significantly simpler than the regeneration of the catalyst in processes of the prior art with regeneration of the exhausted catalyst in the oxydehydrogenation reactor, for which a complicated sequence of regeneration steps, including switching over, depressurization, flushing, burning off, making inert, repressurization and switching over, is required and the catalyst is accordingly exposed to extremely damaging temperature and pressure changes in quick succession.

A capital cost advantage in the order of 40% and a uniform composition of the product stream taken off can be achieved by the mode of operation according to the invention.

Figure 2A:
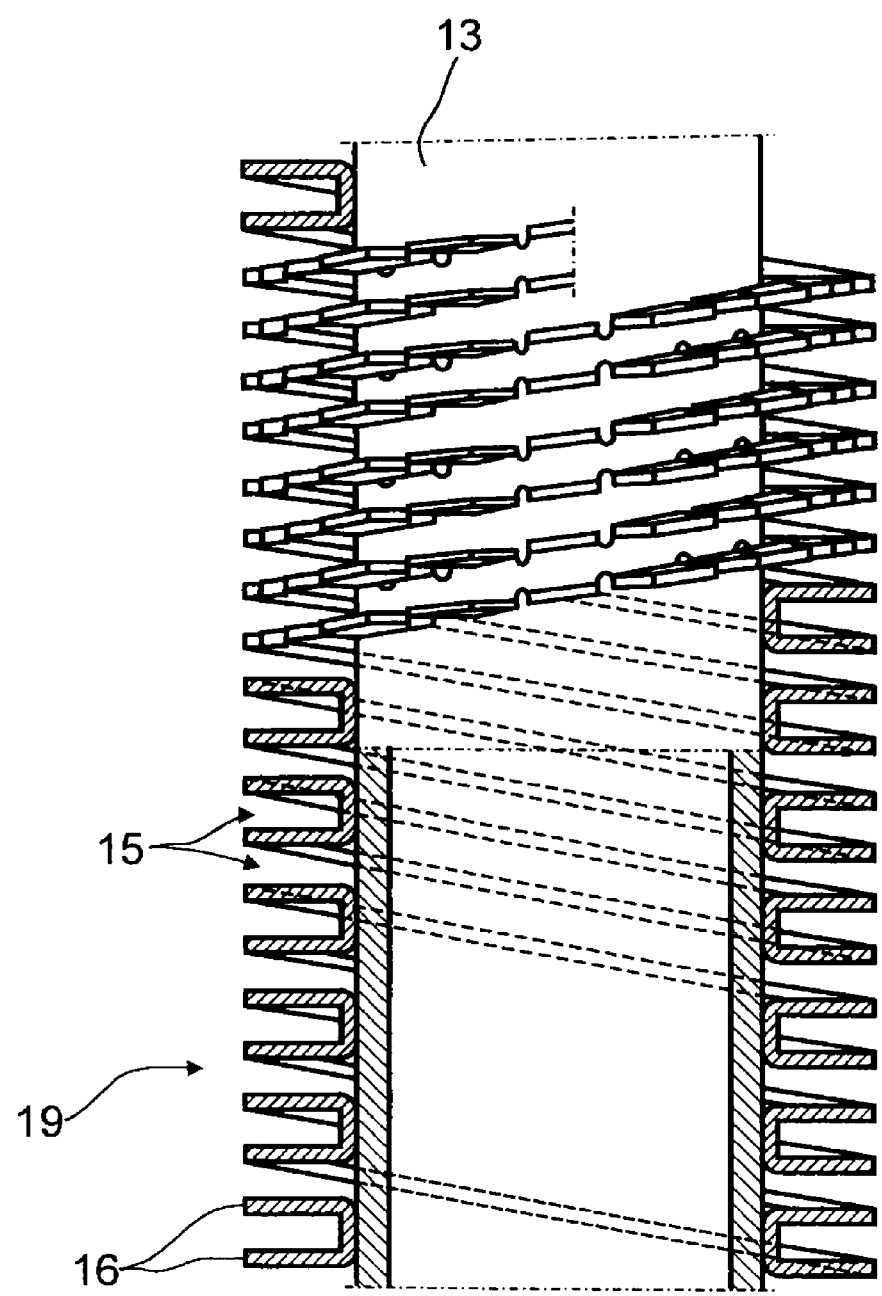
Figure 2B:
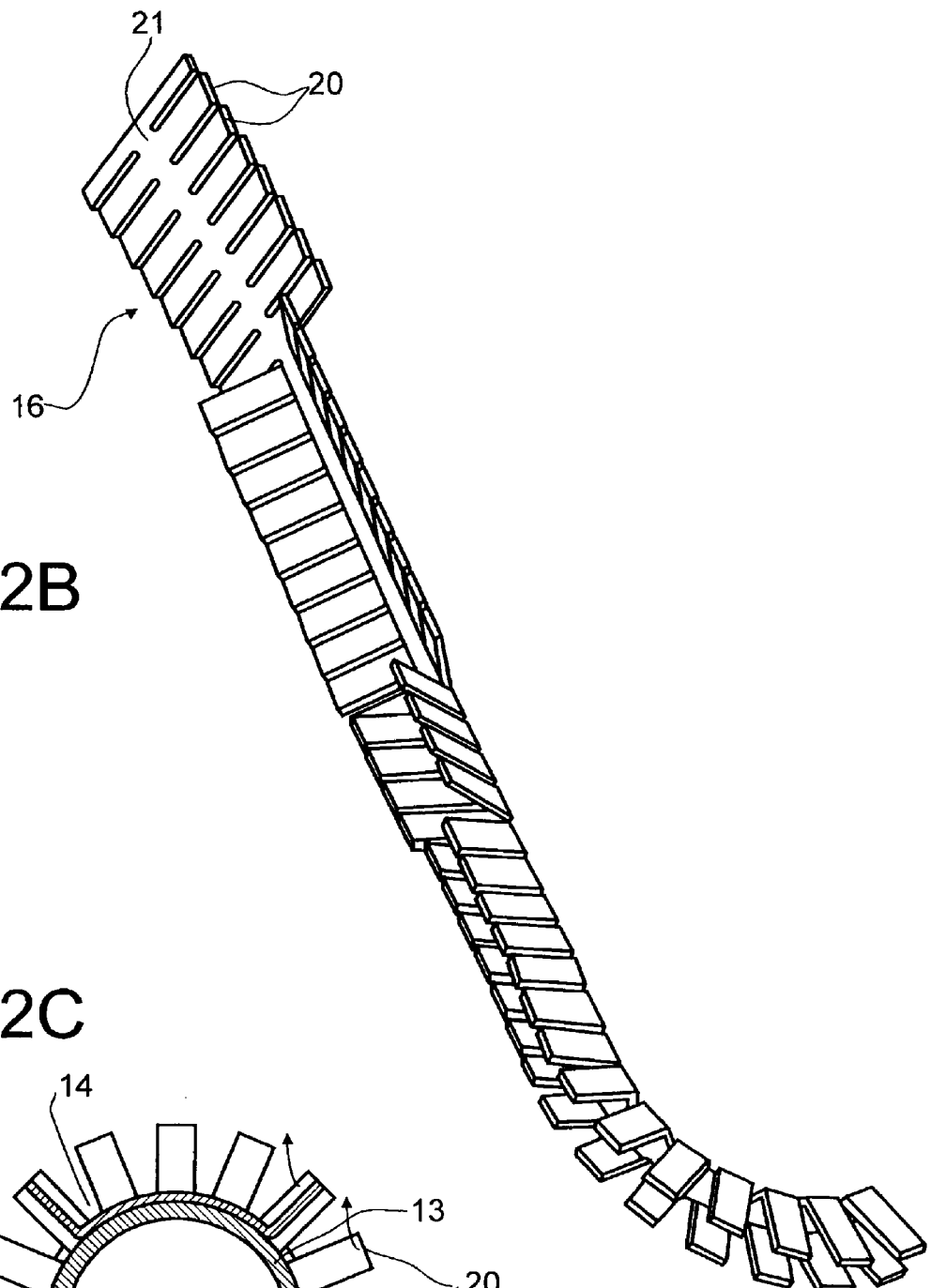
Figure 2C:
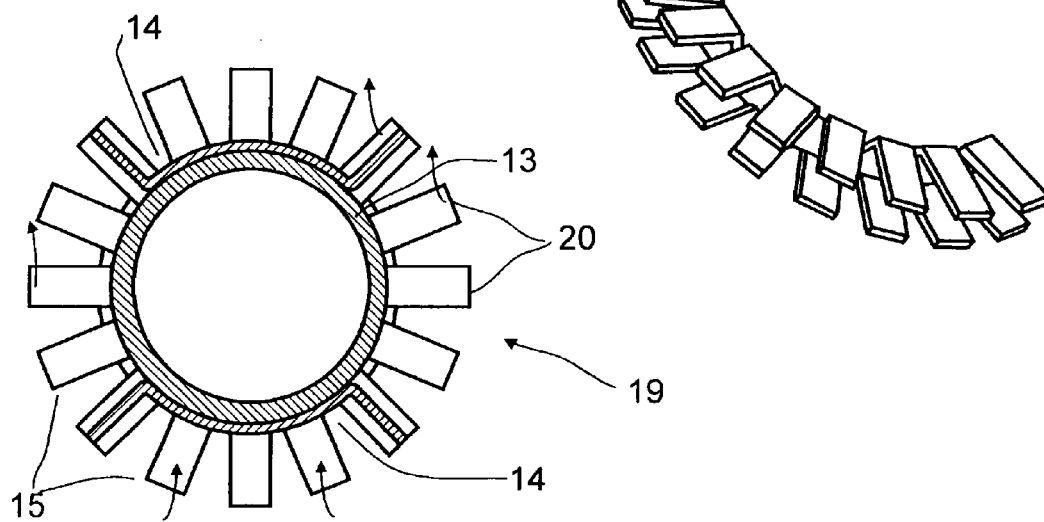
Figure 3:
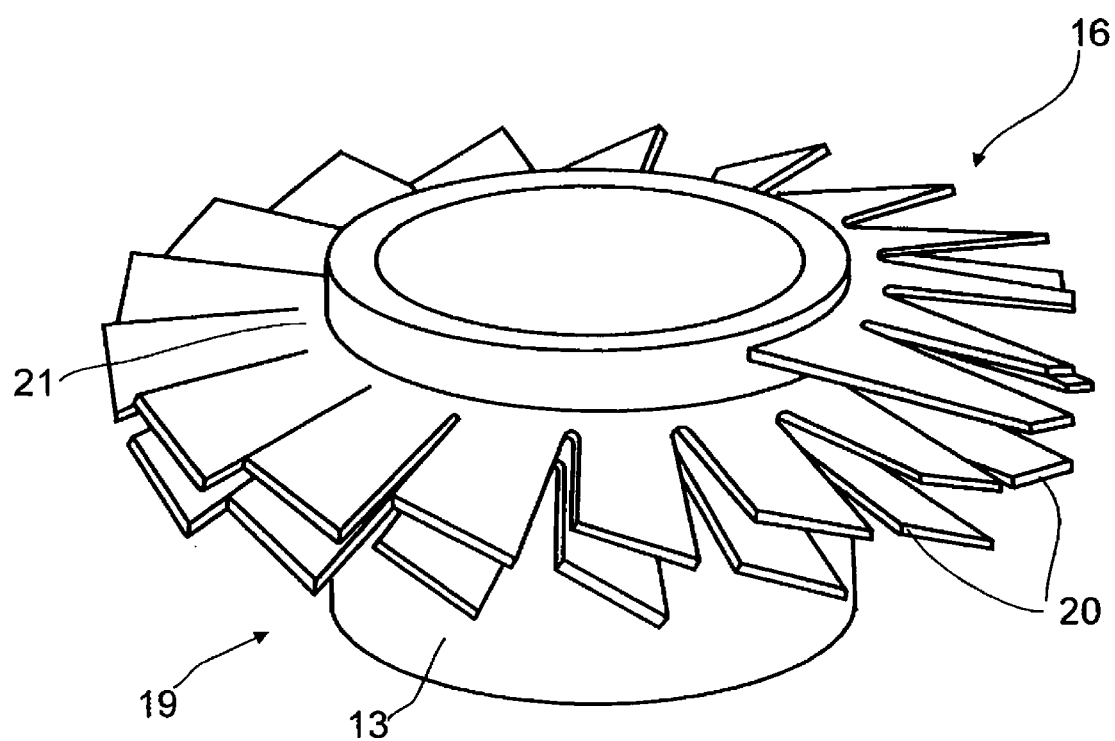
Figure 4A:
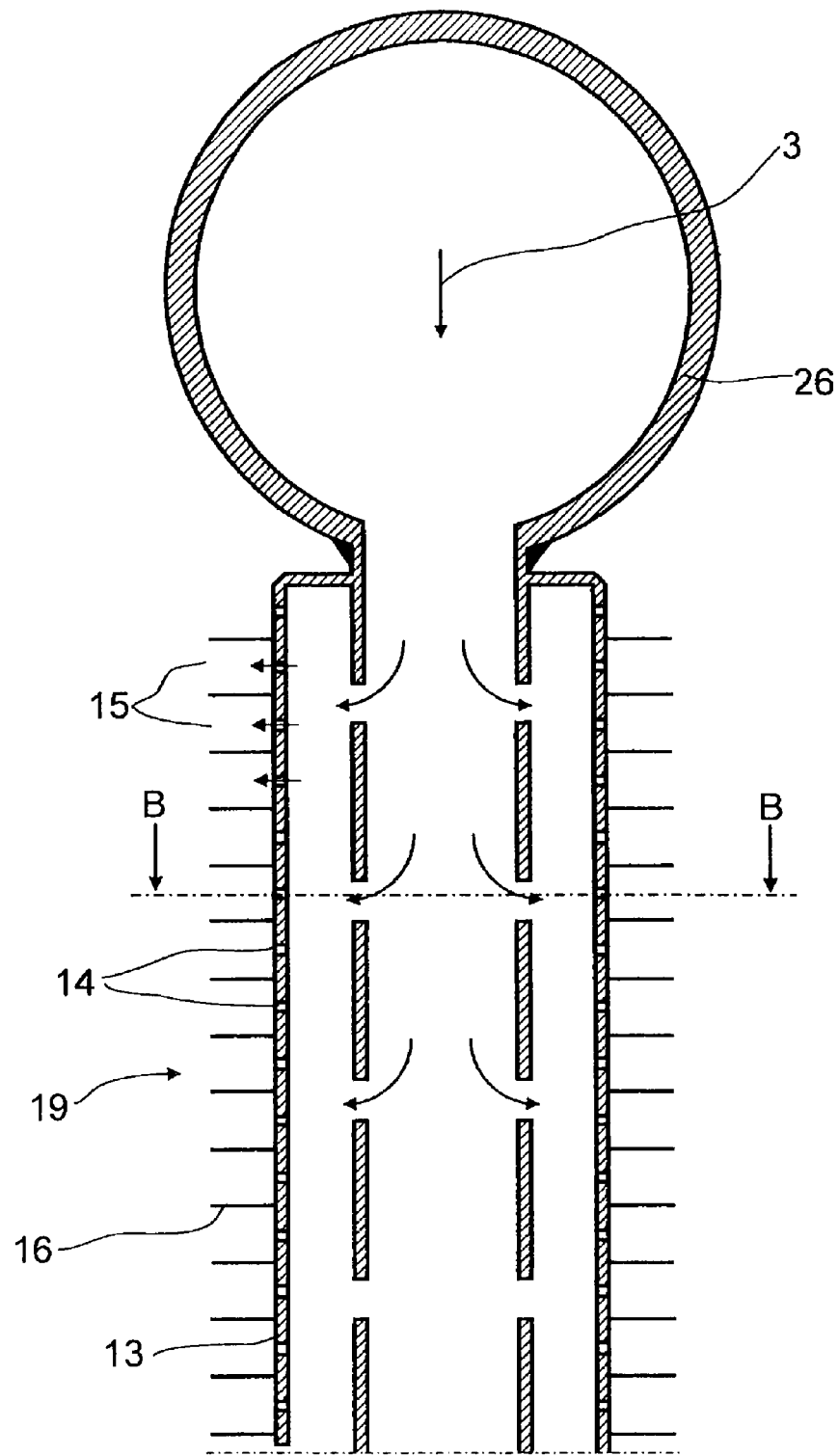
Figure 4B:
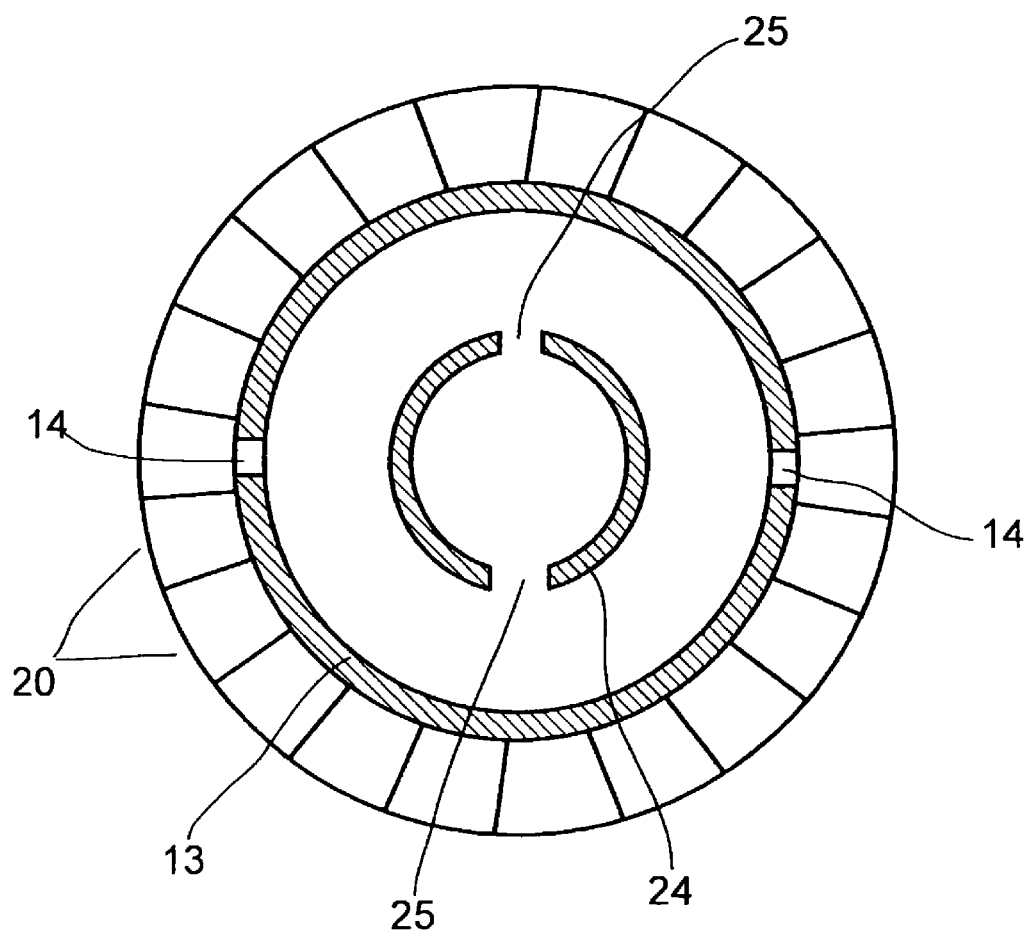
Figure 5:
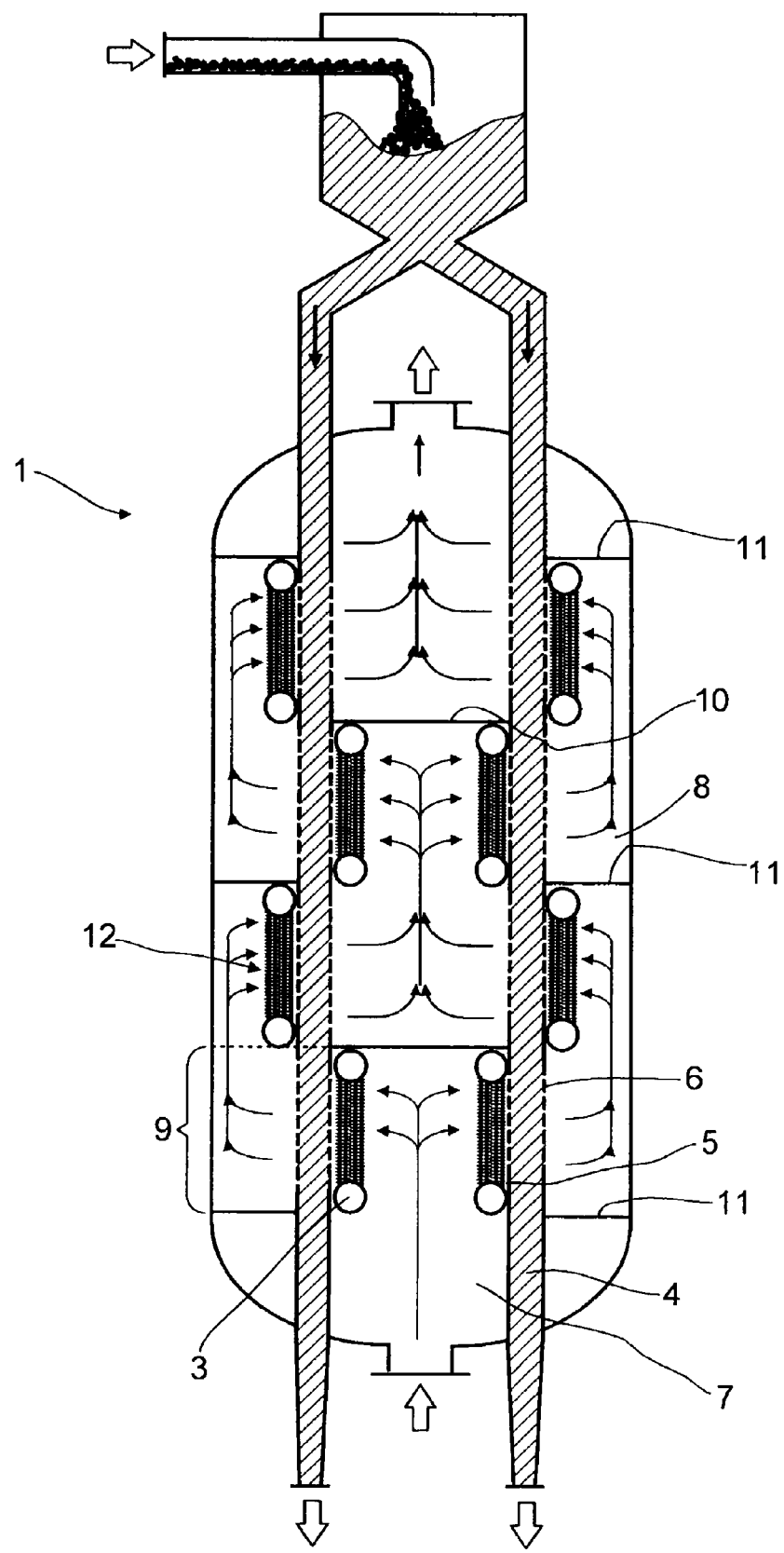
Figure 6:
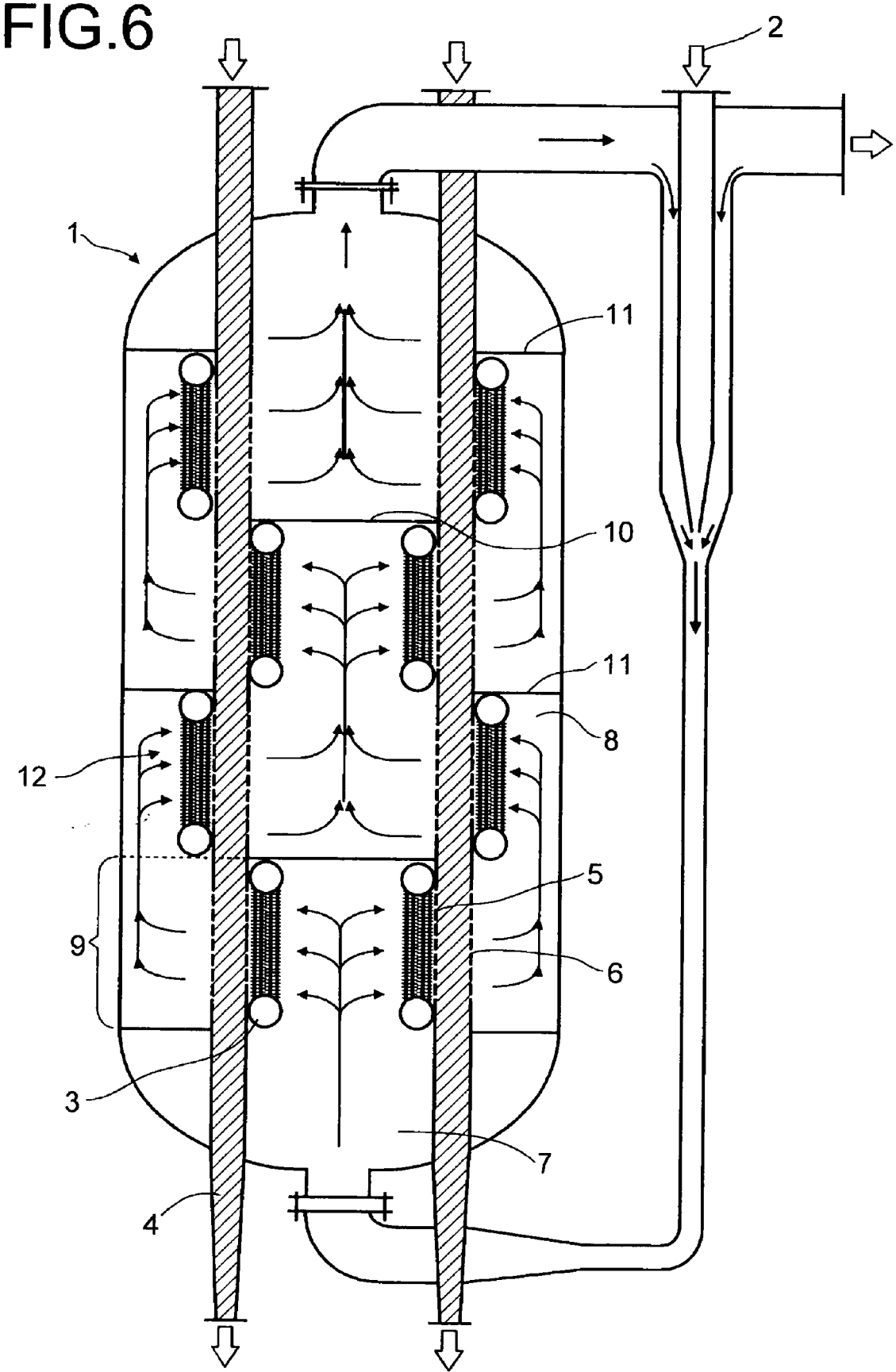
Figure 7:
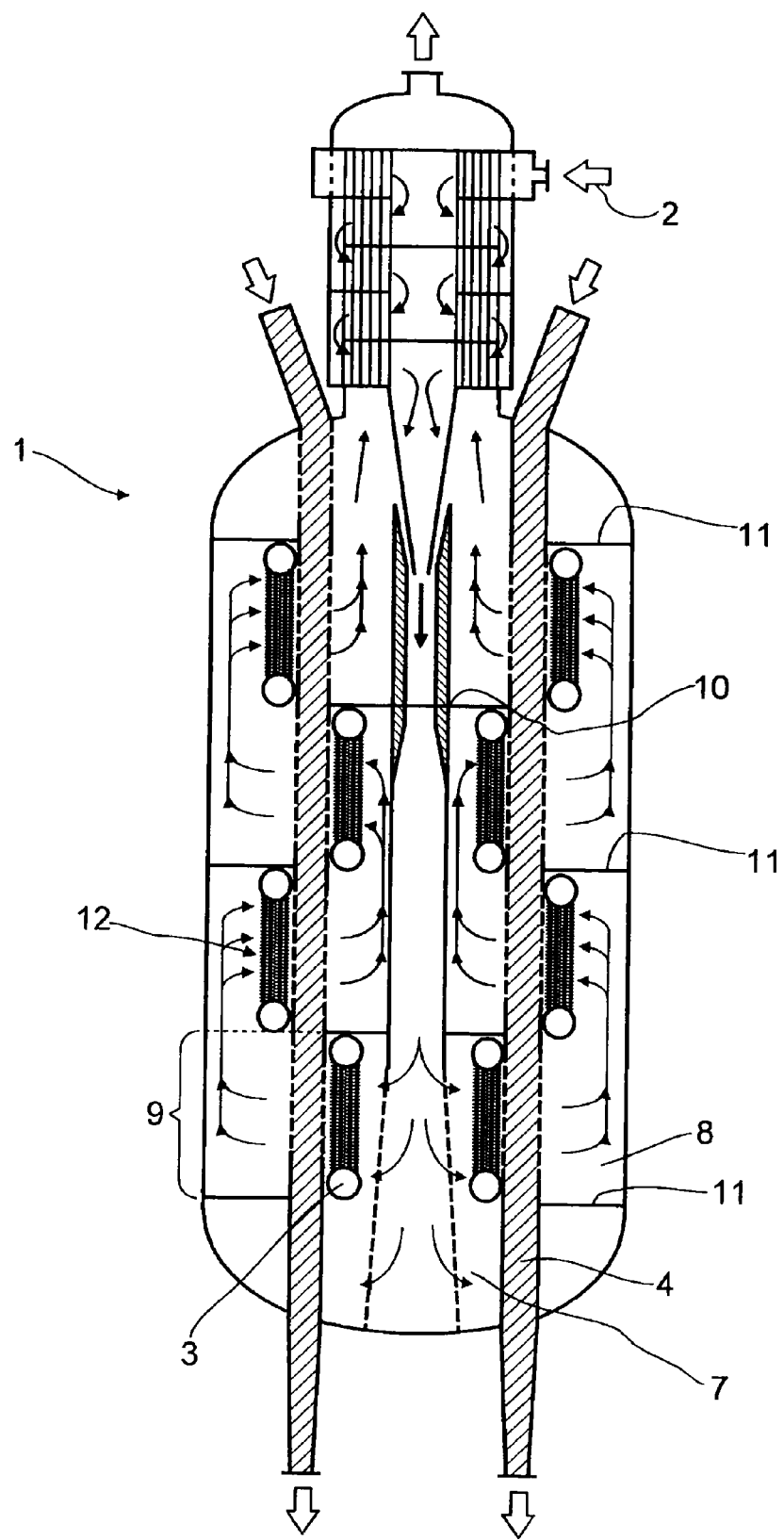

The invention is illustrated below with the aid of a drawing. In the drawing:

FIG. 1 shows a segment of a section through a reactor according invention having a flow direction of the feed gas stream from the outside inward, FIG. 2A shows a detail of a finned tube, with depiction of an individual fin and the procedures for producing it in FIG. 2B and a cross section through a finned tube in FIG. 2C, FIG. 3 shows a perspective view of a finned tube, FIG. 4A shows a longitudinal section through a preferred embodiment of a finned tube, with depiction of a cross section in FIG. 4B, FIG. 5 shows a longitudinal section through an embodiment of a reactor according to the invention, FIG. 6 shows a longitudinal section through a further embodiment of a reactor according to the invention, with recirculation of a substream of the product gas stream, and FIG. 7 shows a longitudinal section through a further embodiment of a reactor according to the invention with preheating of the feed gas stream by means of the product gas stream.

In the figures, identical reference numerals denote identical or corresponding features.

FIG. 1 shows a segment of a cross section through a first embodiment of a reactor 1 according to the invention with introduction of a feed gas stream 2 at the outer wall of the reactor and outflow of this via the interior of the reactor. The feed gas stream 2 impinges perpendicularly onto a mixing-in device 12 comprising two rows of finned tubes 19 which are arranged so that the tubes are located next to the gaps in the other row and are preceded in the flow direction by a first perforated plate 17 and are followed by a second perforated plate 18. The two rows of finned tubes 19 and the upstream perforated plate 17 and the downstream perforated plate 18 are each arranged on concentric circles. The reaction gas mixture which has been premixed in the mixing-in device 12 subsequently flows through the moving catalyst bed 4.

FIGS. 2A to 2C show details of finned tubes 19 having openings 14 which are arranged diametrically opposite one another in the channels 15 between the fins 16 of the finned tubes 19. Here, FIG. 2B shows a fin 16 which is divided by cuts down to a fin base 21 into segments 20 and FIG. 2C shows a cross section through a finned tube 19 with tube 13, channels 15 and segments 20.

FIG. 3 shows a perspective view of a finned tube 19 with tube 13 and helical fin 16 which is divided, with the exception of a continuous fin base 21, into segments 20.

FIG. 4A shows a longitudinal section through a finned tube 19 with tube 13 and fins 16, with openings 14 in the channels 15 between the fins 16 of the finned tubes 19. In the interior of the tube, there is a concentric central plug-in tube 24 which distributes the oxygen-comprising gas stream 3 in the longitudinal direction of the finned tube 13 by means of openings 25 which are arranged diametrically opposite one another and can be seen in the cross-sectional depiction in the plane D-B in FIG. 4B. In FIG. 4A, one end of the finned tube 19 is provided with a ring distributor 26 for the oxygen-comprising gas stream 3.

FIG. 5 shows a longitudinal section through an embodiment of a reactor 1 according to the invention having four reactor sections 9 arranged above one another. The oxygen-comprising gas stream 3 is injected into the feed gas stream 2 via the interior space of the finned tubes 19. The feed gas stream 2 comprising saturated hydrocarbon is fed into the central interior space 7 of the first reactor section 9 and flows via a mixing-in device 12 comprising finned tubes 19 and a perforated plate 17 upstream of this and a downstream perforated plate 18 through a moving bed catalyst 4 installed cylindrically between concentrically cylindrical holding devices 5 and 6. The first reactor section 9 is bounded in subregions, namely in the region of the central interior space 7, by a disk-shaped deflection plate 10 so that the reaction gas mixture leaving the first reactor section 9 flows via the intermediate space 8 at the interior wall of the reactor into the second reactor section 9 located above it. In the second reactor section 9, the mixing-in device 12 is once again located upstream of the moving catalyst bed 4, i.e. in this case concentrically outside the moving catalyst bed. The second reactor section 9 is separated by means of annular deflection plates 11 in the region of the intermediate space 8 at the interior wall of the reactor from the following, third reactor section 9. The sequence of disk-shaped deflection plates 10 and annular deflection plates 11 alternates so that the third reactor section 9 is again bounded at the top by a disk-shaped deflection plate 10 and the fourth reactor section 9 is correspondingly bounded by an annular deflection plate 11.

FIG. 6 shows a longitudinal section through a further embodiment of a reactor according to the invention with recirculation of a substream of the product gas stream.

The embodiment in FIG. 7 additionally has a heat exchanger for heat integration in the upper reactor region, so that the hot product gas preheats the feed gas stream 2 comprising saturated hydrocarbons.

LIST OF REFERENCE NUMERALS 1 reactor
2 feed gas stream
3 oxygen-comprising gas stream
4 moving catalyst bed
5, 6 concentric cylindrical holding devices
7 central interior space
8 intermediate space at the interior wall of the reactor
9 reactor section
10 disk-shaped deflection plates
11 annular deflection plates
12 mixing-in device
13 tubes
14 openings
15 channels
16 fins
17 upstream perforated plate
18 downstream perforated plate
19 finned tubes
20 segments
21 fin base
22 openings in 17
23 openings in 18
24 central plug-In tube
25 openings in 24
26 ring distributor

The invention claimed is:

1. A reactor, comprising an interior wall and an exterior wall, for carrying out a continuous oxydehydrogenation of a feed gas stream of saturated hydrocarbons, comprising a free flow cross section and a flow cross section, after premixing with an oxygen-comprising gas stream over a moving catalyst bed, which is introduced in a longitudinal direction of the reactor between two concentric cylindrical holding devices so as to leave a central interior space and an intermediate space between the moving catalyst bed and the interior wall of the reactor to give a reaction gas mixture, wherein the reactor comprises:

at least reactor sections which are separated from one another by at least one disk-shaped deflection plate arranged alternately in the central interior space and divided into subregions by annular deflection plates arranged in the intermediate space between the moving catalyst bed and the interior wall of the reactor, in each case with a mixing-in device located upstream of the moving catalyst bed in a flow direction of the reaction gas mixture and corn, the mixing-in device comprising:

two or three rows arranged behind one another of tubes which comprise interiors, exteriors, and turbulence generators on said exteriors and constrict the flow cross section for the feed gas stream to from ½ to ⅒ of the free flow cross section, with the oxygen-comprising gas stream being passed through the interiors of the tubes and being injected via openings in the tubes into the feed gas stream;

an upstream perforated plate, upstream of the tubes, comprising openings; and a downstream perforated plate, downstream of the tubes, comprising openings.

2. The reactor according to claim 1, wherein the tubes which comprise turbulence generators are finned tubes, comprising fins, and the openings are arranged in channels between the fins of the finned tubes.

3. The reactor according to claim 1, comprising from 2 to 8 reactor sections.

4. The reactor according to claim 1, wherein the tubes constrict the free flow cross section for the feed gas stream to from ⅓ to ⅙ of original size.

5. The reactor according to claim 2, wherein the finned tubes are formed by tubes comprising a cylindrical exterior and of elongated strips, and are welded along a longitudinal edge of the elongated strips in a spiral fashion onto the cylindrical exterior, wherein the fins are cut with the exception of a fin base to form segments.

6. The reactor according to claim 5, wherein the segments are rotated at an angle to the fin base.

7. The reactor according to claim 2, wherein the finned tubes have from 100 to 300 turns of fins per meter length of the finned tube.

8. The reactor according to claim 2, wherein the external diameter of the tubes is in the range from 25 to 150 mm.

9. The reactor according to claim 2, wherein the ratio of the height of the fins to the external diameter of the tubes is in the range from ⅒ to ½.

10. The reactor according to claim 2, wherein the thickness of the fins is in the range from 0.3 to 1.5 mm and the width of segments is in the range from 3 to 12 mm.

11. The reactor according to claim 2, wherein the second row of finned tubes is arranged so that the tubes are located next to gaps in the first row of finned tubes.

12. The reactor according to claim 11, comprising three rows of finned tubes, with the third row of finned tubes arranged so that the tubes are next to gaps in the second row of finned tubes.

13. The reactor according to claim 2, comprising in each case two openings per channel between the fins of the finned tubes in diametrically opposite positions on the channels, with a minimum distance to the adjacent finned tube in the row of finned tubes.

14. The reactor according to claim 2, wherein the upstream perforated plate is at a distance of 7 to 20 times the diameter of the openings in the upstream perforated plate from an inflow plane of the first row of finned tubes for the feed gas stream.

15. The reactor according to claim 2, wherein the diameter of the openings in the upstream perforated plate is smaller than half of a clear spacing of the fins between two successive turns.

16. The reactor according to claim 1, wherein an opening ratio in the upstream perforated plate, defined as the sum of free areas of the openings in the upstream perforated plate based on total cross-sectional area perpendicular to inflow direction of the feed gas stream into the mixing-in device, is $\leq 0.5$.

17. The reactor according to claim 1, wherein the ratio of upstream or downstream perforated plate thickness to the diameter of the openings in the upstream or downstream perforated plate is in the range from 0.75 to 2.0.

18. The reactor according to claim 2, wherein the downstream perforated plate is located at a distance of from 0.5 to 2 times the diameter of the finned tubes of the last row of finned tubes from the outflow plane of the finned tubes.

19. The reactor according to claim 1, wherein the diameter of the openings in the downstream perforated plate is greater than or equal to the diameter of the openings in the upstream perforated plate.

20. The reactor according to claim 1, wherein the distance from the downstream perforated plate to the entry of the reaction mixture into the fixed catalyst bed corresponds to from 5 to 20 times the diameter of the openings in the downstream perforated plate.

21. A process for carrying out a continuous oxydehydrogenation of a feed gas stream of saturated hydrocarbons, wherein the process is carried out in a reactor according to claim 1.

22. The process according to claim 21, wherein the feed gas stream comprises propane or butane.

23. The process according to claim 21, wherein the oxygen-comprising gas stream is air or technical grade oxygen.

24. The process according to claim 21, wherein a substream of the reaction gas mixture from the last reactor section in flow direction is recycled into the first reactor section.

25. The process according to claim 21, wherein the feed gas stream is preheated by indirect heat transfer from the reaction gas mixture leaving the last reactor section.

26. The reactor according to claim 1, wherein an opening ratio in the upstream perforated plate, defined as the sum of free areas of the openings in the upstream perforated plate based on total cross-sectional area perpendicular to inflow direction of the feed gas stream into the mixing-in device, is $\leq 0.3$.

* * * * *